(12) United States Patent
Ohno et al.

(10) Patent No.: US 7,241,616 B2
(45) Date of Patent: Jul. 10, 2007

(54) SYSTEM FOR CULTURING HUMAN CELLS AND TISSUES

(75) Inventors: Tsuneya Ohno, Tokyo (JP); Kikuo Hirasawa, Tokyo (JP); Masanobu Hattori, Kawagoe (JP)

(73) Assignees: Jikei University School of Medicine, Tokyo (JP); Hirasawa Works, Tokyo (JP)

( * ) Notice: Subject to any disclaimer, the term of this patent is extended or adjusted under 35 U.S.C. 154(b) by 468 days.

(21) Appl. No.: 10/458,559

(22) Filed: Jun. 10, 2003

(65) Prior Publication Data

US 2003/0232429 A1    Dec. 18, 2003

(30) Foreign Application Priority Data

Jun. 17, 2002   (JP)   ............... 2002-175238

(51) Int. Cl.
*C12M 1/00* (2006.01)
*C12M 3/00* (2006.01)
*C12M 1/22* (2006.01)

(52) U.S. Cl. .............. 435/303.1; 435/305.2; 435/307.1; 435/308.1; 435/809; 454/63; 454/59; 219/407; 119/311; 600/21; 600/22; 312/236; 237/3

(58) Field of Classification Search .......... 435/303.1, 435/809; 454/59, 63
See application file for complete search history.

(56) References Cited

U.S. PATENT DOCUMENTS

| | | | | |
|---|---|---|---|---|
| 4,262,091 A | * | 4/1981 | Cox ................... 435/253.6 |
| 5,749,967 A | * | 5/1998 | Sakauchi et al. ............ 117/200 |
| 5,861,305 A | * | 1/1999 | Silley et al. ............. 435/286.6 |
| 5,958,763 A | * | 9/1999 | Goffe ....................... 435/303.1 |
| 6,151,536 A | * | 11/2000 | Arnold et al. ............... 700/237 |
| 6,255,103 B1 | * | 7/2001 | Tamaoki et al. ......... 435/303.1 |
| 6,532,399 B2 | * | 3/2003 | Mase ........................ 700/237 |
| 2002/0137197 A1 | * | 9/2002 | Ammann et al. ........ 435/287.2 |
| 2003/0090364 A1 | * | 5/2003 | Cardinale et al. .......... 340/5.54 |
| 2003/0203479 A1 | * | 10/2003 | Cecchi .................... 435/303.1 |
| 2005/0266392 A1 | * | 12/2005 | Tamaoki et al. ............... 435/2 |

FOREIGN PATENT DOCUMENTS

DE    10017192 A1  *  10/2001

OTHER PUBLICATIONS

English translation of DE 10017192 A1, Oct. 11, 2001, Fazler et al.*

* cited by examiner

*Primary Examiner*—Gladys JP Corcoran
*Assistant Examiner*—Nathan Bowers
(74) *Attorney, Agent, or Firm*—Kilyk & Bowersox, P.L.L.C.

(57) ABSTRACT

Disclosed is a human cell/tissue culturing system including a plurality of incubators, each incubator capable of aseptically storing/culturing cell(s) or tissue(s) derived from a (human) individual and identifying the cell(s) or the tissue(s) during incubation, wherein each incubator comprises a detector corresponding to an individual key, the response of the detector permitting opening/closing of a door of each incubator, the response of the detector of one incubator triggering the interception of the function of the detector(s) of other incubator(s) to consequently inhibit opening/closing of the door(s) of the other incubator(s).

7 Claims, 4 Drawing Sheets

SYSTEM FOR CULTURING HUMAN CELLS AND TISSUES

The present application claims priority from Japanese Patent Application No. 200-175238, filed Jun. 17, 2002, incorporated by reference herein.

BACKGROUND OF THE INVENTION

1. Field of the Invention

The present invention relates to a human tissue culturing system and to an instrument ($CO_2$ incubator) for culturing tissue(s) keeping the system. The present invention relates to a simple means for preventing the possible contamination of individual(s) and excluding the mixup when human tissue(s) or cell(s) is/are cultured.

2. Description of the Related Art

Tissues and cells derived from a mammal such as human are routinely cultured using a $CO_2$ incubator. Cells such as myocardial cells, dendritic cells, hematopoietic stem cells and neural stem cells derived from human are cultured as the autograft of human cell(s)/tissue(s) is realized. Each cell is proliferated in a $CO_2$ incubator, and is processed for use in a clean bench. This culture is very strictly controlled. It is sometimes required that cells derived from one patient are treated in one room or that the treatment are carried out by two workers in order to prevent the contamination between cells during culturing and processing. Carrying out these regulations in a practical hospital, however, requires the construction of a large-scale facility, makes the business very complex, and makes it very difficult to culture self-cells to transplant.

SUMMARY OF THE INVENTION

The present invention was conceived in view of the above situations. It is therefore the object of the present invention to provide a system and an apparatus that minimize the possibility of the miswork in order to simply and safely achieve the culturing of cells for autografting a human tissue or the like.

To achieve the above object, the present invention provides:

1. A human cell/tissue culturing system including a plurality of incubators, each incubator capable of aseptically storing/culturing cell(s) or tissue(s) derived from a (human) individual and identifying the cell(s) or the tissue(s) during incubation, wherein each incubator comprises a detector corresponding to an individual key, the response of the detector permitting opening/closing of a door of each incubator, the response of the detector of one incubator triggering the interception of the function of the detector(s) of other incubator(s) to consequently inhibit opening/closing of the door(s) of the other incubator(s).

2. A human cell/tissue culturing system according to claim 1, wherein the detector corresponding to the key of the incubator carries such a regulation function as to allow the function of the detector of other incubator to be interrupted even when the key is drawn out.

3. A human cell/tissue culturing system according to claim 1 or 2, wherein the key is capable of responding to a detector of a clean bench that permits controlling of the initiation of the use in the clean bench during the treatment in the clean bench in which cell(s) or tissue(s) derived from human(s) is/are taken out from an incubator.

4. A human cell/tissue culturing system according to any one of the preceding claims, wherein the key is an electric key, and wherein the detector for detecting the key is an electric detector.

5. An instrument for culturing tissue(s), the instrument keeping the function of the human cell/tissue culturing system according to any one of points 1 to 4 above.

DESCRIPTION OF THE PREFERRED EMBODIMENTS

Culturing human cell(s)/tissue(s) is a method for isolating a tissue, an organ, a lymphocyte, a fertilized egg or a dendritic cell derived from human or a fused cell prepared from a dendritic cell and a tumor cell, followed by proliferating cell(s) in a culture vessel such as flask and petri dish, wherein the vessel usually contain cell(s) derived from human, a medium, a human or fetal calf serum, and so on. The incubation is usually carried out at a temperature of 37° C. at a $CO_2$ concentration of 5% (or 3% if desired) and a saturated humidity. The $CO_2$ incubator is an instrument that was developed to maintain an environment suitable for culturing cell(s) or tissue(s). For example, the temperature is a condition that is physiologically necessary for proliferation of cell(s). A concentration of $CO_2$ is set to stably maintain the pH of a medium necessary for the proliferation of cell(s). Sodium hydrogen carbonate ($NaHCO_3$) added to regulate a concentration of proton in culture medium is dissociated as follows: $2NaHCO_3 \leftrightarrows Na_2CO_3 + H_2O + CO_2$. Emission of $CO_2$ results in the increase in $Na_2CO_3$, and pH becomes 7.4 or higher, and the high pH causes a trouble in culturing a cell. To prevent the trouble, $CO_2$ gas is supplied into the $CO_2$ incubator to reconvert $Na_2CO_3$ to $NaHCO_3$, and pH of the medium can be equilibrated between 7.1 and 7.4.

A lid of flask or the like for culturing human cell(s) or tissue(s) must be loosened to supply $CO_2$ gas in the incubator into the culture flask and exchange the air. If water evaporates from the medium in the culture flask during incubation, the salinity of the medium is changed to remarkably affect the conditions for culturing the cell(s). It is necessary to humidify inside the $CO_2$ incubator in order to prevent the drying. The humidification is usually carried out by making the atmosphere of the incubator in a saturation state by spontaneously evaporating water in a vat in the $CO_2$ incubator. Moreover, it is also necessary to circulate air to the $CO_2$ incubator.

Figure 1:
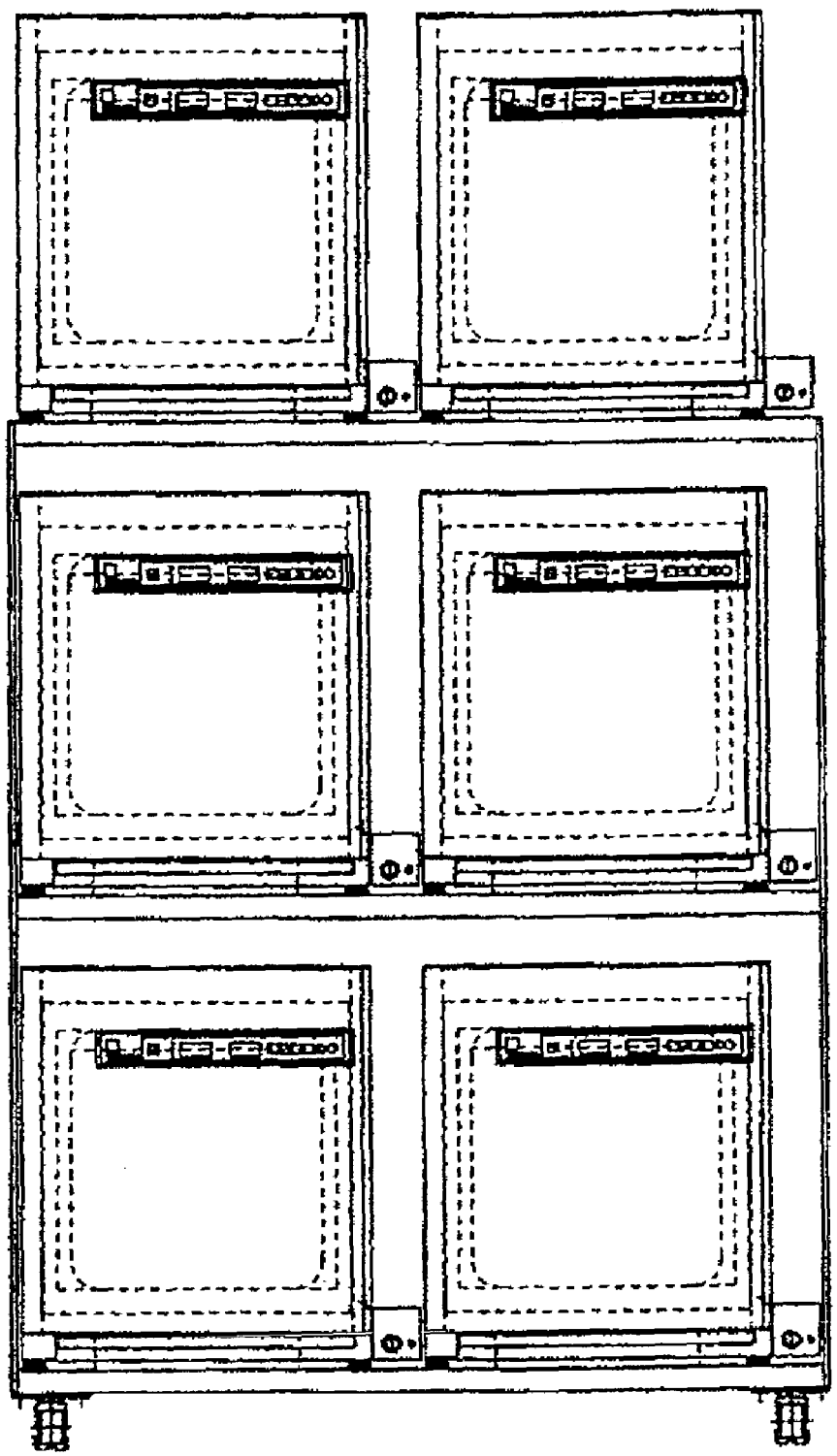
FIG. 1 illustrates a set of incubators.

In the present invention, the $CO_2$ incubator as described above is recognized as one incubator for culturing cell(s) derived from one individual. The law requires that cell(s) derived from one individual are cultures in one incubator. Therefore, incubators are usually arranged vertically and horizontally like cube-type lockers (FIG. 1). Each incubator has a function of regulating environmental culture conditions such as gas composition by supplying the above gas. The control function can be carried out by a central management system or individually.

Cell(s) or tissue(s) derived from human (s) is/are aseptically stored/cultured in each incubator, and the cell(s) or tissue(s) can be individually identified in association with a computer or simply by a manual operation during incubation. The present invention is a cell-culturing system in which incubators are controlled, wherein each incubator has a detector corresponding to characteristic and individual key by which identification is carried out with a computor or manually. When specific cell(s) is/are processed, it becomes necessary to open/close, with a key, an incubator in which the specific cell(s) is/are stored/cultured, wherein the key corresponds to each incubator in which a detector that can respond to each key is installed. Response of the detector permits opening/closing a door of each incubator.

In case a door is unlocked with response to the detector of one incubator, functions of all other detectors that are controlled are blocked as a result of synchronization, so that other doors are locked.

A detector corresponding to a specific key of a specific incubator can carry such a regulation function that a function of the detector of other incubator can be blocked by drawing out the key. Such a function permits detecting a key with a detector installed in a clean bench to permit using the clean bench under control in case a specific key is drawn from a specific incubator to keep the identification of a clean bench when cells are taken out of an incubator to aseptically process them in a clean bench or the like. Therefore, it is a preferred embodiment as a system of the present invention to install a detector that permits identifying a key also for a clean bench.

Although an electric key, a magnetic key and an optical key are preferably used for a key according to the present invention, other keys can also be used. An electric key is most suitable considering that it is not preferable that current flows in an instrument used for culturing human cells, and that an electric key is simple and reliable. An electric detector, a magnetic detector, an optical detector or the like is installed corresponding to the type of the key.

A method for generally controlling incubators with a key system according to the present invention is installed in an instrument as a system to provide an instrument for culturing tissue(s) having a function as a useful and reliable system for culturing human cell(s)/tissue(s).

EXAMPLES

The present invention will now be described in more detail by way of examples. These examples are however to be regarded as a help in concrete recognition, and the scope of the present invention is not intended to be limited by the examples which follow.

Example 1

Set of Incubators

FIG. 1 illustrates the front view of a practical state in which incubators according to the present invention are collectively managed. A monitor for identifying an individual and monitoring culture conditions is installed on the upper part of each incubator. A detector, which is a key box, is installed in the lower right part of each incubator.

Example 2

Figure 2:
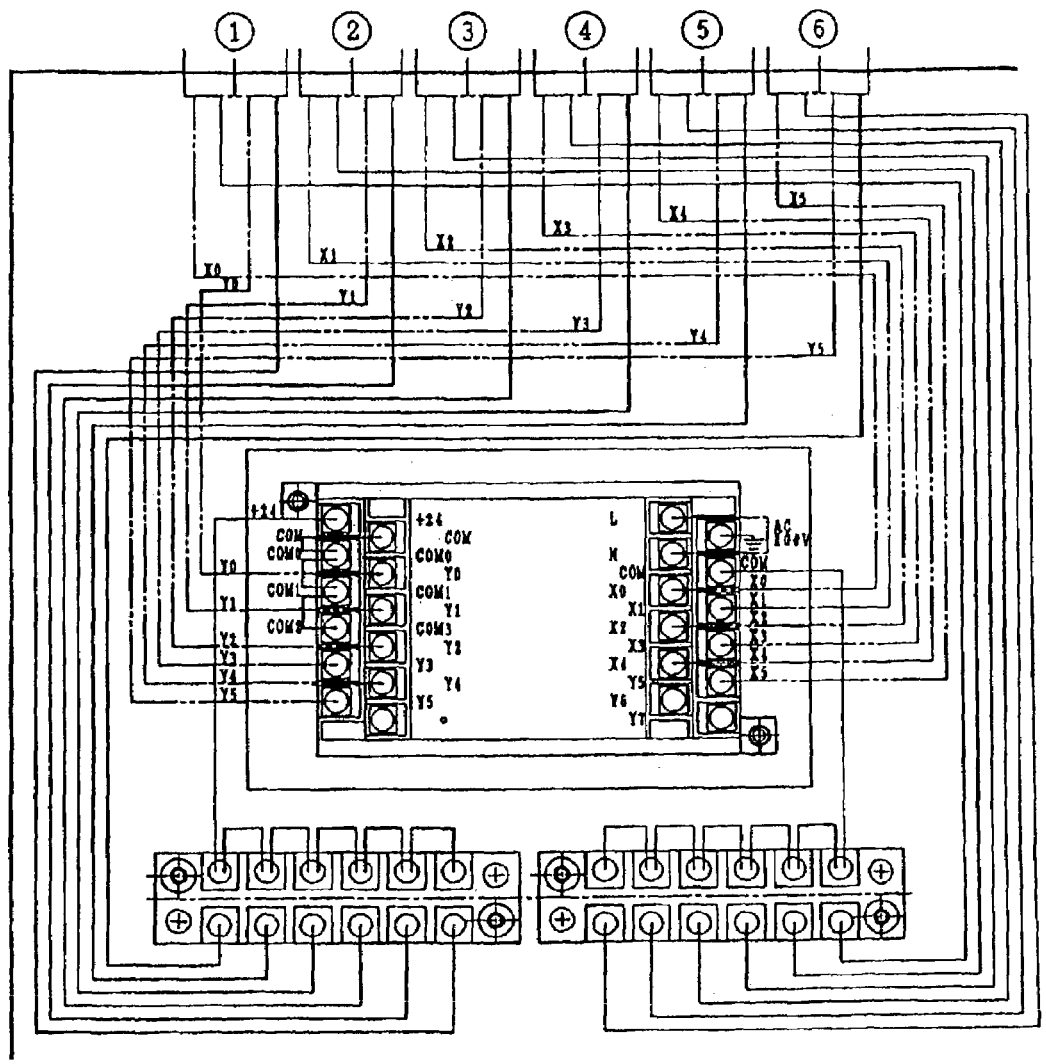
FIG. 2 is a wiring diagram.
Figure 3:
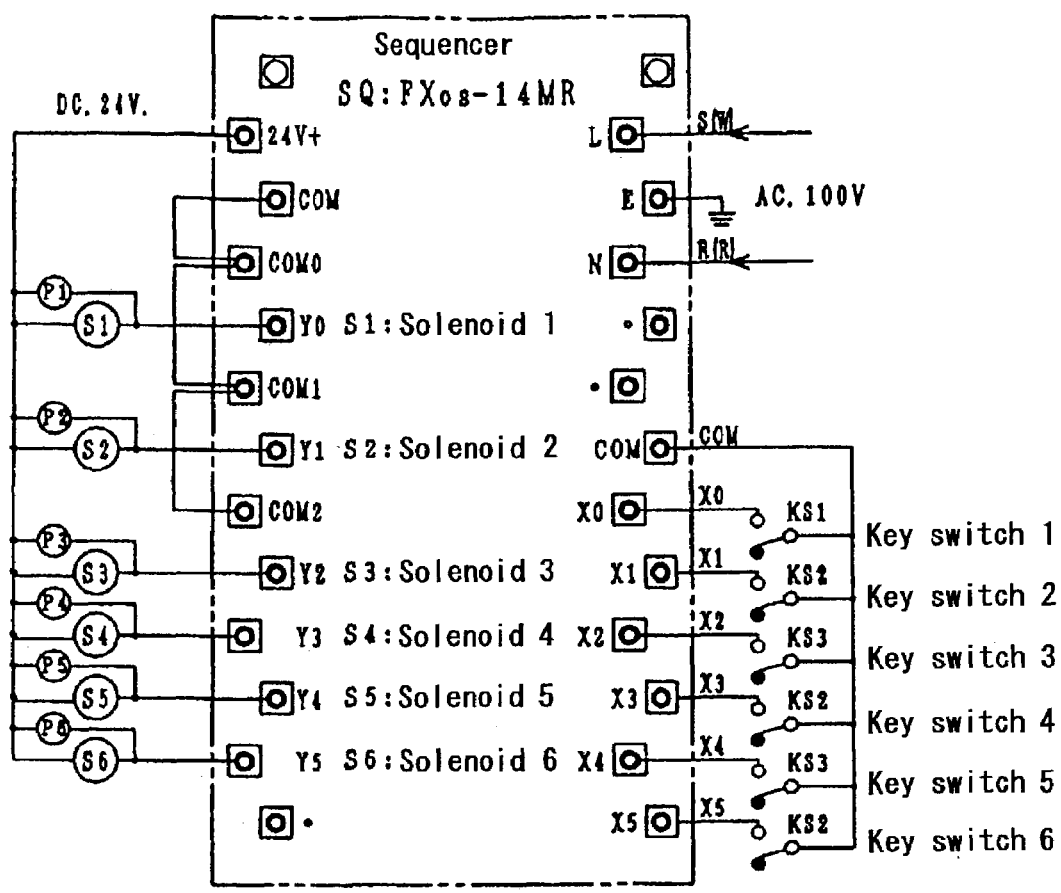
FIG. 3 is a wiring diagram.
Figure 4:
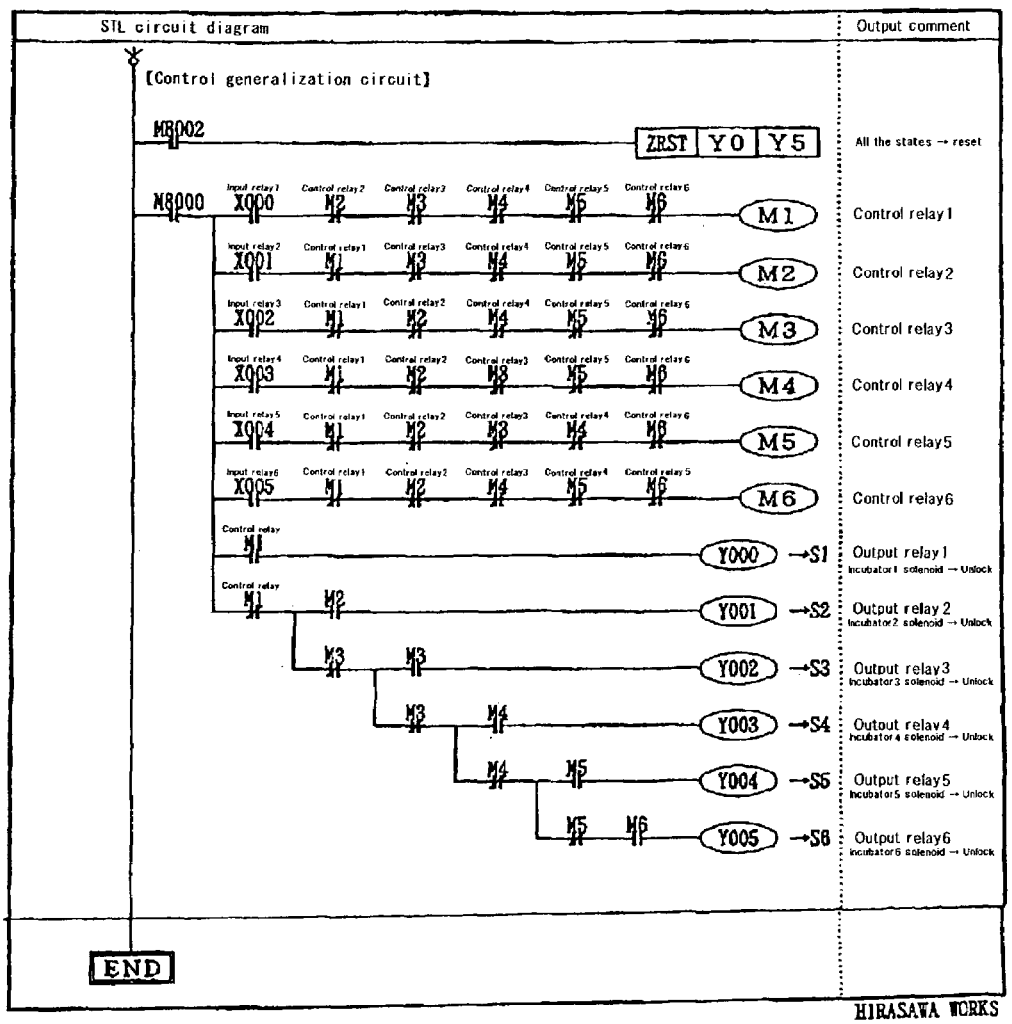
FIG. 4 is a sequence circuit diagram.

FIGS. 2 and 3 illustrate charts of interlock-control circuit. When one key is turned right to be ON, a corresponding solenoid unlocks a rod from a hole of an outer door to permit opening/closing the door of the corresponding incubator. Such a regulation circuit that makes operation of key switches of five other incubators ineffective at that time is written in a sequencer. Therefore, it becomes impossible to open/close the outer doors of five other incubators. FIG. 4 illustrates a sequencer control circuit. When input relay X000 is input (key switch 1 is ON), for example, the regulation relay becomes ON. In addition, when regulation relays M2–M6 are all OFF (key switches 2–6 are OFF), M1 becomes ON. When each key switch becomes ON, each corresponding control relays M1–M6 become ON. Only when all the control relays M2–M6 are OFF, when key switch 1 becomes ON, control relay 1 becomes ON. For each output relays (Y000–Y005), when M1 is ON, Y000 becomes ON to open the outer door. When each of regulation relays M2–M6 becomes ON, an outer door of each corresponding incubator is unlocked.

Symbols and codes in figures are described below:

①–⑥ mean incubators.

X0–X7 mean sequencer input symbols. For example, X0 controls the key switch of $CO_2$ incubator 1. When key X0 is pushed, the key switch of $CO_2$ incubator 1 becomes ON. The same applies to the other keys. X6 and X7 are spares. '1' is sometimes expressed as '001' in Figures using a three-digit system. Others are also sometimes expressed in a similar manner.

Y0–Y7 mean sequencer output signals. For example, Y0 is a lock solenoid for $CO_2$ incubator 1, and is output to S1. $CO_2$ incubator 1 is locked by this.

COM means a sequencer input signal and is an input-side common terminal.

COM0–COM3 mean sequencer output signals and are output-side common terminals 0–3.

ZRST has a function of resetting all of relays Y0–Y5, and is reset for safety when the power supply is ON.

M8002 means a special relay that momentarily becomes ON when a sequencer is energized.

M8000 means a special relay that becomes ON when a sequencer is energized.

Symbol 1

'⊣ ⊢' means an ON(a) junction that becomes ON when each relay (each of X, Y and M can be assigned) is energized.

Symbol 2

'⊣/⊢' means an OFF(b) junction that becomes OFF when each relay (each of X, Y and M can be assigned) is energized.

'+24' means a plus terminal of a DC 24V service power supply.

'L' means a sequencer power supply connection terminal.

'N' means a sequencer power supply connection terminal.

(It works at an arbitrary voltage between AC 100V and 240V between terminals L and N.)

'Sequencer' is a computor only for a control circuit. Writing in by a predetermined method (symbol) permits controlling the circuit.

'SQ' means sequencer.

'FXOS-14MR' is a sequencer made by Mitsubishi Electric Corp.

'DC.24V' means DC 24 V.

'+24V' means a plus side of DC 24 V.

'S1'–'S6' mean solenoids 1–6, wherein 'solenoid' means an electric part so designed as a rod moves by an electromagnetic power made by a magnetic coil against a power of a spring. This output relay unlocks each $CO_2$ incubator.

'LE30-13' is a solenoid made by Dakigen Corp.

'KS1'–'KS6' mean key switches 1–6 that become ON/OFF with keys.

'S-187-90-E-1' is a key switch made by Dakigen Corp.

'P1'–'P6' mean signal lights 1–6 that light when solenoids are energized.

'S(W)' means one phase of an AC power supply, wherein 'W' means white covered wire.

'R(R)' means another phase of an AC power supply, wherein 'R' means red covered wire.

'E' means earth.

'MC1–6' mean metal plug sockets 1–6, wherein 'metal plug socket' means a metallic, electric part that is used for connect a flexible cord and can be fixed usually with a metallic screw cap.

'NCS-1604RP' is a metal plug socket made by Nanahoshi Science Laboratory.

The present invention can provide a practical means that permits very efficiently, very simply and individually managing/culturing human cell(s), and is extremely useful for practically culturing human tissue(s).

What is claimed is:

1. A human cell/tissue culturing system comprising a plurality of incubators, and a control circuit each incubator capable of aseptically storing/culturing cell(s) or tissue(s) derived from an individual and identifying the cell(s) or the tissue(s) during incubation, wherein each incubator comprises a detector corresponding to an individual key, the response of the detector permitting opening/closing of a door of each incubator, the response of the detector of one incubator triggering the interception of the function of the detector(s) of other incubator(s) using said control circuit to consequently inhibit opening/closing of the door(s) of the other incubator(s), wherein the detector corresponding to the key of the one incubator carries such a regulation function as to allow the function of the detector of the other incubator(s) to be interrupted with said control circuit even when the key of the one incubator is drawn out.

2. The human cell/tissue culturing system according to claim 1, wherein the system further comprises a clean bench comprising a detector that recognizes the individual key and that controls the initiation of the use in the clean bench during the treatment in the clean bench in which cell(s) or tissue(s) derived from human(s) is/are taken out from an incubator.

3. The human cell/tissue culturing system according to claim 1, wherein the key is an electric key, and wherein the detector for detecting the key is an electric detector.

4. A processing system for culturing tissue(s), comprising the human cell/tissue culturing system of claim 1, wherein the processing system comprises a computer system and said computer system controls the function of the human cell/tissue culturing system.

5. The human cell/tissue culturing system according to claim 2, wherein the key is an electric key, and wherein the detector for detecting the key is an electric detector.

6. A processing system for culturing tissue(s), comprising the human cell/tissue culturing system of claim 2, wherein the processing system comprises a computer system and said computer system controls the function of the human cell/tissue culturing system.

7. A processing system for culturing tissue(s), comprising the human cell/tissue culturing system of claim 3, wherein the processing system comprises a computer system and said computer system controls the function of the human cell/tissue culturing system.

* * * * *